United States Patent [19]

Prosl et al.

[11] Patent Number: 4,541,429
[45] Date of Patent: Sep. 17, 1985

[54] IMPLANTABLE MAGNETICALLY-ACTUATED VALVE

[76] Inventors: Frank R. Prosl, Duxbury; James G. Skakoon, Norwood; Gerard S. Carlozzi, Pembroke, all of Mass.; Infusaid Corporation, 02, Norwood, Mass.

[21] Appl. No.: 376,686

[22] Filed: May 10, 1982

[51] Int. Cl.$^4$ .................... A61M 29/00; A61F 1/00
[52] U.S. Cl. ..................... 604/249; 623/11; 137/625.65; 251/129.21; 128/1 R
[58] Field of Search .......... 128/350 V, 1 R, DIG. 25; 251/65, 84, 141, 139; 3/1; 604/9, 10, 33, 249, 246; 137/47, 625.65

[56] References Cited
U.S. PATENT DOCUMENTS

| 3,315,660 | 4/1967 | Abella . | |
|---|---|---|---|
| 3,495,620 | 2/1970 | Raimondi et al. | 3/1 X |
| 3,570,806 | 3/1971 | Sturman | 251/65 |
| 3,659,600 | 5/1972 | Merrill . | |
| 3,675,171 | 7/1972 | Kirk | 251/65 |
| 3,856,044 | 12/1974 | Caldwell | 137/625.5 |
| 4,076,045 | 2/1978 | Nakajima et al. | 251/141 |
| 4,463,969 | 8/1984 | Harrison | 251/141 |

FOREIGN PATENT DOCUMENTS

| 1586044 | 3/1981 | Fed. Rep. of Germany . |
| 1008888 | 11/1965 | United Kingdom . |
| 1237295 | 6/1971 | United Kingdom . |
| 1360823 | 7/1974 | United Kingdom . |
| 1376641 | 12/1974 | United Kingdom . |
| 2039000 | 11/1982 | United Kingdom . |
| 2003586 | 12/1982 | United Kingdom . |

Primary Examiner—Richard J. Apley
Assistant Examiner—David J. Isabelle
Attorney, Agent, or Firm—Cesari and McKenna

[57] ABSTRACT

A miniature implantable magnetically actuated valve relatively insensitive to normally-encountered shock loads includes a housing for containing a movable ferromagnetic valve member. Inlet and outlet passages are provided in the housing at least one of which has an internal valve seat which is engageable by the valve member to close that passage. The valve member is resiliently suspended within the housing by special flat multiply-started spiral springs which permit the valve member only a single degree of freedom toward and away from the valve seat. The valve member is biased in one direction or the other and the valve is actuated transcutaneously by a magnet juxtaposed to the valve outside the body which produces a magnetic force on the valve member which exceeds and opposes the biasing force.

8 Claims, 4 Drawing Figures

IMPLANTABLE MAGNETICALLY-ACTUATED VALVE

This invention relates to an implantable medical device. It relates more particularly to an implantable valve which can be actuated transcutaneously.

BACKGROUND OF THE INVENTION

Relatively recently there have been developed various implantable devices for administering infusate such as heparin, insulin and other medicaments over a prolonged term. Examples of such implantable infusion apparatus are disclosed in U.S. Pat Nos. 3,951,147 and 4,193,397.

In many applications of apparatus of this general type, it becomes necessary to change the infusate dosage to the patient on a temporary basis. For example, in the case of an insulin administering device or artificial pancreas, or it is desirable that the patient receive a continuous basal dose of infusate. Then, after a meal when the patient's sugar level rises, a larger or bolus dose of infusate should be administered to counteract the increased sugar level in the patient's blood caused by the ingestion of the food.

This increased dosage may be provided in a variety of ways. For example, in an implantable device such as depicted in the aforementioned U.S. Pat. No. 4,193,397, a single infusate reservoir is provided and infusate is drawn from that reservoir at two different rates to provide the two different dosages. Alternatively, the device may have separate reservoirs containing infusate in different concentrations. Infusate from one or another of these reservoirs is delivered to the infusion site in the patient's body depending upon the circumstances. In either case, however, provision must be made for actuating a valve implanted in the patient's body to establish the two different infusate flows to the infusion site in the patient's body.

Conventionally, such implantable valves are actuated in three different ways. More particularly, as shown in U.S. Pat. No. 4,013,074, a valve can be implanted subcutaneously and provided with a mechanical actuator situated directly under the skin. The valve is opened or closed, as the case may be, by finger pressure on the skin which depresses the actuator. While such a valve may operate satisfactorily, the digital deflection of the patient's skin pinches the skin which may cause valve site tissue damage and discomfort to the patient. Also in some valves of this type, a feedthrough is required in the valve to transmit motion from the valve actuator to the valve interior.

The second type of implantable valve employs a solenoid or piezoelectric crystal to actuate the valve. Finger depression of a subcutaneous button switch connected between the solenoid or crystal and a battery opens and closes the valve. Also, by the use of telemetry, remote actuation of a solenoid or a crystal to open and close the valve can be performed. This type prior valve is disadvantaged in that it requires an implanted battery and ancillary circuitry to provide electrical power to actuate the valve. Such electrical components cannot tolerate autoclaving and the battery must be replaced from time to time necessitating an operation on the patient. Also, as with the first type valve, the skin may be pinched to depress the actuating switch.

The third type of implantable valve is actuated transcutaneously by positioning an external magnet opposite the implanted valve. Such valves are depicted, for example, in U.S. Pat. Nos. 3,315,660 and 3,659,600. A complete magnetically actuated valved infusate pump is disclosed in U.S. Pat. No. 4,152,098. While these prior magnetically actuated devices perform their functions, they do have certain drawbacks which militate against their wider use and application.

More particularly, some prior valves are overly large, particularly in the axial direction which is the direction of valve member movement. Consequently, when implanted under the skin, they penetrate a relatively great distance into body tissue causing patient discomfort. Some valves which are relatively small employ valve member suspension systems which do not flex sufficiently to permit a proper fluid flow rate, or if they do, the components of the suspensions suffer fatigue failure after a relatively short time, requiring valve repair or replacement.

Also some such conventional valves are prone to actuation prematurely upon sudden accelerations of the patient's body as when he jumps up and down or is jostled. Prior attempts to alleviate that problem have resulted in valves having valve member suspension systems which are so stiff that an overly large, unwieldly external actuating magnet is required in order to develop sufficient magnetic force to open or close the valve transcutaneously.

Still further, some prior valves of this third type require slidable valve feedthroughs connected between the valve actuator and the movable valve member. Such sliding or rubbing surfaces are prone to becoming bound up and worn. Also, they generate small particles which can degrade valve operation and become entrained in the infusate being dispensed to the patient, with obvious deleterious consequences.

There are other procedures in which conduits are provided in the body to conduct fluid from one location in the body to another. For example, hydrocephalic shunts are implanted in the body to drain fluid from the cranial cavity to relieve pressure on the brain. Implanted continence devices are also proposed. In all of these devices, it would be desirable to have the option of providing a valve for controlling flow through the conduit that can be actuated extracorporally.

SUMMARY OF THE INVENTION

Accordingly, the present invention aims to provide an improved implantable magnetically actuated valve.

Still another object of the invention is to provide a miniature, magnetically actuated valve which can be located directly under the skin without penetrating appreciably into the patient's body tissue.

A further object of the invention is to provide such a valve which is neither actuated nor harmed by sudden motions of the patient's body.

A further object of the invention is to provide a valve of this type which has no electrical components or wear surfaces so that it can remain implanted in the patient's body for a prolonged period of time.

Another object of the invention is to provide an implantable valve which does not produce particulate matter which may be entrained in the infusate flowing through the valve.

Still another object is to provide such a valve which when implanted can be actuated transcutaneously by means of a small magnet spaced appreciably from the valve.

A further object is to provide such a valve which can withstand autoclaving.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, our implantable valve is designed so it may be used to control the flow of fluid through a variety of devices and prostheses implanted in the body including those enumerated above. However, here, we will describe it in conjunction with an implantable infusate reservoir to controlledly dispense infusate to a selected site in an animal or human body.

The valve comprises a flat, wafer-like housing having an inlet passage and an outlet passage which are in fluid communication through a valve seat. A ferromagnetic valve member is supported within the housing opposite the valve seat by a special suspension to be described later. Suffice to say at this point that the valve member is movable between a closed position wherein it engages the valve seat thereby isolating the valve inlet and outlet passages and an open position wherein it is spaced from the seat permitting fluid to flow through the valve.

The present valve differs from others of this general type primarily in its mode of suspending and biasing the movable member which opens and closes the valve. More particularly, that member is suspended by one or more special, flat annular cantilevered springs. For most applications, two such rings are preferable. One edge of each annular spring is secured to a housing wall and the other spring edge is connected to the valve member. Each flat spring is formed with a plurality of generally parallel, spiral slits extending between its edges thereby forming a plurality of flat spiral spring arms. These arms are quite flexible in the axial direction, but very stiff in the rotational and radial directions thus allowing the valve member only a single degree of movement in the axial direction toward and away from the valve seat.

The spring construction thus prevents unwanted movements of the valve member rotationally and laterally so that the valve member does not rub against the valve seat causing excessive wear of that part. Yet, this plural spiral arm construction gives each spring a low spring constant in the axial direction. Therefore, the spring force does not become appreciably larger as the spring is flexed which feature facilitates valve actuation as will be described presently.

The valve member is normally biased along the valve axis in one direction or the other so that it has an intrinsic bias position, i.e., either seated or unseated. However, instead of using the spring suspension to provide that intrinsic bias, a ferromagnetic body is mounted to the valve housing opposite the valve member. This biasing body is positioned and polarized so that it urges the valve member toward its reference or bias position, e.g., against the valve seat so that the valve is normally closed. The bias force is sufficiently strong that normally-encountered shock loads do not unseat the valve. The valve member is moved to its opposite position by means of a ferromagnetic member such as a permanent magnet juxtaposed to the valve outside the patient's body. The attraction (or repulsion) between the external actuating magnet and the ferromagnetic valve member is sufficiently strong to overcome the internal bias and to maintain the valve member in its opposite position. As soon as the external magnet is removed, the valve member returns to its intrinsic bias position.

Since the spring suspension has a very low axial spring rate, the spring force does not become appreciably larger with spring deflection. Accordingly, a relatively small magnetic actuating force is able to move the valve member a sufficient distance away from the valve seat to open the valve without the spring force exceeding that actuating force.

Since the valve member is the only moving part in the valve and is supported by simple flexures, there are no friction or rubbing surfaces which can wear out or generate particles which might be entrained in the fluid passing through the valve. Even the valve member itself is prevented from rubbing against its seat as described previously. Therefore the valve is not prone to failure and can remain implanted for a prolonged period without causing discomfort to the patient.

Resultantly, the present valve addresses simultaneously all of the mutual antagonistic requirements in such a valve of very small size, sufficiently high flow rate, a low valve member spring rate, immunity from normally-encountered shock loads and a long life.

BRIEF DESCRIPTION OF THE DRAWING

For a fuller understanding of the nature and objects of the invention, reference should be had to the following detailed description, taken in connection with the accompanying drawing, in which.

DESCRIPTION OF THE PREFERRED EMBODIMENT

Figure 1:
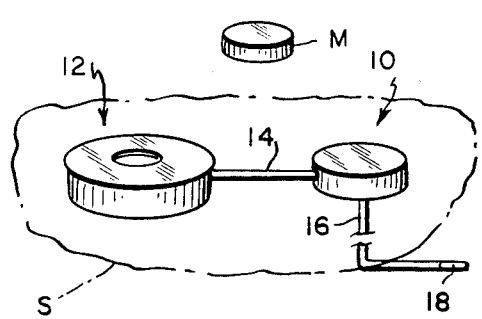
FIG. 1 is a diagrammatic view of an implantable magnetically actuated valve made in accordance with this invention, shown in conjunction with an implantable infusate reservoir.

Referring first to FIG. 1 of the drawing, the valve indicated generally at 10 is shown implanted directly under the skin S of an animal or human body. The valve is connected to receive the infusate output from an implanted infusate reservoir 12 by way of an inlet tube 14. An outlet tube 16 leads from the valve 10 to a catheter 18 situated at a selected site in the patient's body. The reservoir 12 is not part of this invention so it will not be described in detail. Preferably, it is of the self powered type disclosed in U.S. Pat. Nos. 3,951,147 and 4,193,397. Suffice it to say that the reservoir normally supplies liquid infusate under pressure to valve 10.

The valve of the invention can be normally open or normally closed. The valve 10 specifically illustrated is the latter so that normally no infusate is delivered to catheter 18. Valve 10 is opened, when appropriate, by positioning magnet M directly adjacent the skin S opposite the valve site. Magnet M can be either a permanent magnet or an electromagnet. If desired, a spot can be tattooed on the skin to mark that location. The magnetic force exerted by the magnet M actuates an internal valve member, thereby opening the valve permitting fluid to flow from the reservoir 12 to the catheter 18. As soon as the magnet M is removed from the vicinity of the valve 10, the valve closes, thereby shutting off further flow of infusate to the body site.

Figure 3:
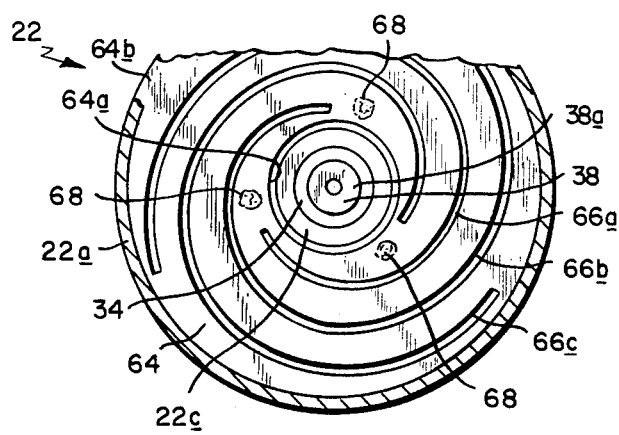
FIG. 3 is a sectional view along line 3—3 of FIG. 2 with parts broken away.
Figure 2:
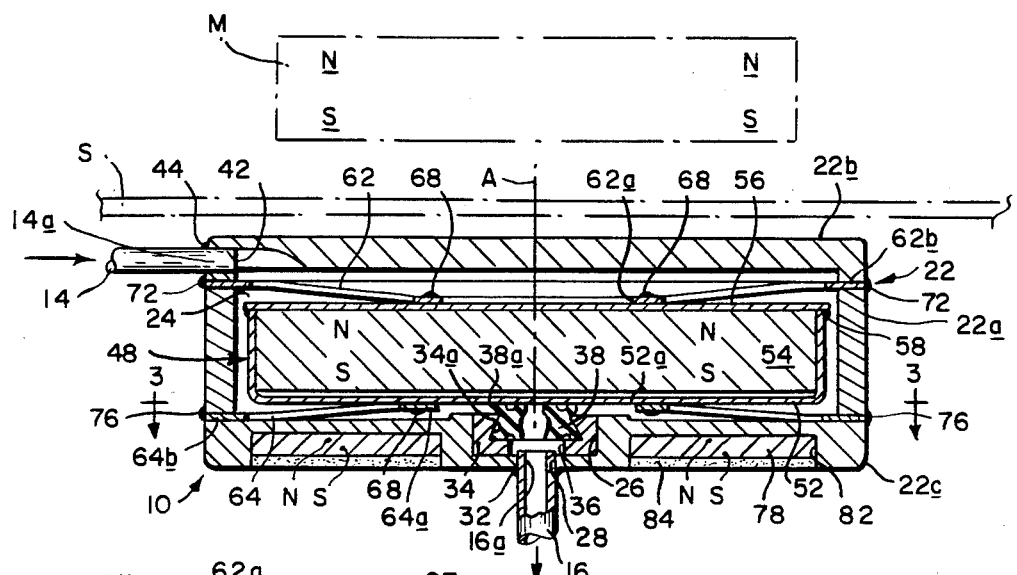
FIG. 2 is a view in medial section on a much larger scale of the valve depicted in FIG. 1.

Referring now to FIGS. 2 and 3, the valve 10 comprises a flat wafer-like housing shown generally at 22 made of titanium or other material compatible with the human system. The housing is composed of a tubular section 22a which forms the side wall of the housing, an upper discoid section 22b which forms the top wall of the housing and a lower discoid section 22c which forms the housing bottom wall. Together the sections define a generally cylindrical housing cavity 24. Typically, the housing has a thickness of about 0.30 inch and a diameter of about 0.88 inches, giving it a total exterior value of about 0.18 cubic inches.

Formed on the inside wall of the bottom section 22c is a generally cylindrical recess 26 which is coaxial with the valve axis indicated at A in FIG. 2. The bottom wall of the recess 26 is formed with an opening 28 which snugly receives the end 16a of the outlet tube 16. The tube end 16a is secured to section 22c by a weld bead 32 which extends all around the boundary between those two elements. Snugly seated in recess 26 is a cylindrical titanium collet 34 having a central opening 36 which is colinear with tube 16. The collet has a counterbore 34a which is tapered inward toward the top of the collet to grasp a resilient seal 38 whose outer wall is tapered to mate with the collet counterbore. The seal 38 is preferably a ring seal having an X-shaped cross-section such as is sold by Minnesota Rubber Co. under its trademark Quad-X. This type seal provides a pair of concentric resilient sealing areas at its upper surface 38a which forms the valve seat.

As best seen in FIG. 2, an opening 42 is machined through the side of the upper housing section 22b to receive the end 14a of the inlet tube 14. The tube is permanently secured to that section by a weld bead 44 extending all around the boundary between the tube and the housing section.

Figure 4:
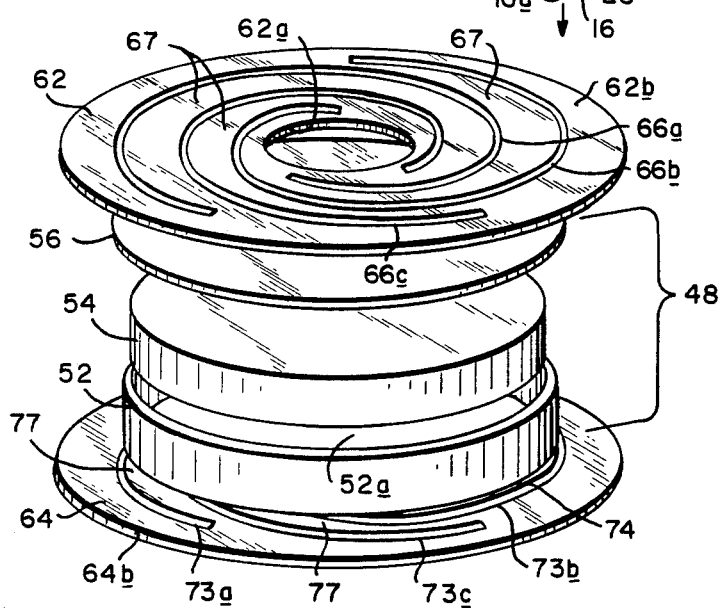
FIG. 4 is an exploded perspective view illustrating a section of the valve in greater detail.

Positioned in the housing cavity 24 is a movable ferromagnetic valve member shown generally at 48. As shown in FIGS. 2 and 4, the valve member comprises a flat cylindrical can 52 having an open top. Seated in the can is a ferromagnetic body 54 specifically illustrated as an axially polarized, discoid permanent magnet. Magnet 54 is a very strong and very small wafer-like magnet, typically composed of a rare earth material such as samarium-cobolt. The magnet is hermetically sealed within the can by a discoid cover 56 which is seated on the rim of the can and permanently connected thereto by a weld bead 58 extending all around the can at the boundary between the cover and the can rim. Preferably, the can and its cover are made of the same material as the housing, i.e., titanium.

The valve member 48 is suspended within the housing by special upper and lower, flat, annular, titanium springs 62 and 64. As shown in FIGS. 2 and 4, spring 62 has an inner edge 62a and an outer edge 62b. Extending between those inner and outer edges is a plurality, herein three, generally parallel spiral slits 66a, 66b and 66c. Each slit starts near one spring edge, e.g., outer edge 62b and terminates adjacent its other edge , i.e., edge 62a, extending around the spring approximately 360 degrees in the process. Furthermore, the beginnings and ends of the three slits are distributed at equal angles about the spring, i.e. 120 degrees apart.

As best seen in FIG. 2, the spring 62 is connected near its inner edge 62a to the valve member cover 56 by three spot welds 68 which are situated adjacent the inner ends of the slits 66a to 66c. These welds are shown in FIG. 4 with respect to lower spring 64. The outer edge 62b of spring 62 is connected to the housing side wall. Conveniently, this is done when assembling the housing by sandwiching the spring edge 62b between the housing sections 22a and 22b and then applying a weld bead 72 all around the boundary between those sections, which bead also captures the spring edge 62b, as seen in FIG. 2.

The three slits thus form in the spring 62 three, generally parallel, flat, spiral, cantilevered spring arms 67 which extend between the housing wall and the valve member.

Referring now to FIGS. 2 to 4, the flat annular spring 64 has an inner edge 64a and an outer edge 64b. Extending between these edges are three parallel spiral slits 73a, 73b and 73c which are in all respects similar to the slits 66a to 66c in spring 62. The slitted spring is secured to the bottom wall 52a of can 52 by three spot welds 68 (FIG. 3) which are located adjacent the inner ends of the three slits. The outer edge 64a of the spring is captured between the housing side wall section 22a and the bottom section 22c and a weld bead 76 is formed all around the joint between those sections to permanently connect them together. Thus the spring slits 73a to 73c form three, parallel, spiral, cantilevered spring arms 77 which help to suspend the valve under 48.

It should be noted that the diameter of the inner spring edge 64a is appreciably larger than that of the seal 38 so that when the valve member is in its closed position, the can bottom wall 52a can seat on the seal surface or seat 38b thereby completely blocking the opening through the seal and isolating the valve inlet and outlet passages.

In the valve specifically illustrated, the springs 62 and 64 have the same spring rate so that they tend to support the value members 48 centrally within housing cavity 24. However, means are provided for biasing that member toward the valve seat 38b. In the illustrated valve, the biasing means is an axially polarized annular magnet 78 permanently secured in an annular recess 82 formed in the underside of the housing bottom section 22c. Magnet 78 is oriented so that its north pole is positioned opposite the south pole of magnet 54 so that the magnet 78 pulls magnet 54, and thus the can bottom wall 52a, toward the valve seat 38b. Preferably, the magnet 78 is potted in a suitable material 84 (FIG. 2) such as epoxy resin which is compatible with the human system.

The normally-closed valve specifically illustrated here is actuated or opened by positioning magnet M directly opposite the valve 10 with its south pole facing the valve as shown in FIG. 2. The attractive force between the magnet M and the valve member magnet 54 is sufficient to offset the biasing force due to the presence of the biasing magnet 78 so that the valve member 48 is moved away from the valve seat 38a permitting infusate to flow from reservoir 12 through the valve cavity 24 and outlet tube 16 to the catheter 18. The flow continues as long as the magnet M remains in that position. As soon as magnet M is removed to the position illustrated in FIG. 1, for example, the valve member 48 returns to its closed position due to the attractive force developed between the magnet 54 and the biasing magnet 78, thereby stopping fluid flow through the valve.

Primarily because of the plural spiral arm design of springs 62 and 64 which suspend valve member 48 within the housing, the present valve is able to satisfy simultaneously all of the desirable criteria for an implantible valve discussed above. Each spring can flex a sufficient distance in the direction of the valve axis A to operate the valve. For example, a titanium spring have an ID of 0.25 inch, an OD of 0.88 inch, an arm width of 0.06 inch and a thickness of 0.005 inch can be deflected in the order of 0.075 inch repeatedly without yielding or suffering fatigue failure.

In addition, the springs have a low spring constant in the axial direction. Therefore the spring force never becomes larger than the magnetic valve actuating force over the complete travel of the valve member 48. On the other hand, the springs 62 and 64 are quite stiff rotationally as well as in the radial or lateral direction so that the valve member 48 does not rub against the valve seat 38*a* and cause wear that might impair the proper operation of the valve. In a typical valve, for example, that member is deflected laterally only 0.001 inch or less under a 10*g* radial shock load. At the same time, the bias magnet 78 is sufficiently strong to prevent normally-encountered axially directed shock loads from unseating the valve member.

Still further, the springs 62 and 64 permit the valve to function frictionlessly with only one moving part. This eliminates frictional or rubbing surfaces which promote wear and the production of debris in the valve, thereby ensuring a long, trouble-free valve life after implantation. Finally, the springs permit all of the aforesaid advantages to be incorporated into a valve having a very small outer envelope, typically in the outer of seven-eighths inch in diameter and one-quarter inch thick. Therefore the implanted valve can be accommodated in a very small space just under the patient's kin without causing appreciable tissue damage or discomfort to the patient.

In some applications, certain changes may be made to the valve specifically illustrated herein. For example, the ferromagnetic body 54 component of the valve member can be an iron disk. In this event, however, a stronger external magnet M may be required to actuate the valve. Conversely, the employment of a magnet 54 in the valve member of sufficient size or strength would permit the valve to be actuated by a nonmagnetized external ferromagnetic body such as an iron block.

Further, while the valve 10 specifically illustrated herein is a normally-closed valve, it should be understood that the valve can just as well be normally open. To accomplish this, the biasing magnet 78 is simply inverted so that the valve member 48 is normally biased to its open position. Then, when it is desired to close the valve temporarily for one reason or another, the magnet M, also inverted, is positioned opposite the valve so that it repels the valve member magnet 54 and thus closes the valve so long as the magnet M remains in that position. In fact, in many applications, this arrangement wherein the valve operates in a repelling mode is preferable also in that an actual magnet is required to move the valve member. Therefore, unlike the case of the valve 10, there is no chance of the valve being actuated inadvertently if the patient should lean against a large ferromagnetic object such as an iron door.

Also the valve made in accordance with this invention can have a variety of porting configurations other than the illustrated one. For example, the valve can have two outlets and two valve seats, one in the top wall 22*b* and the other in the bottom wall 22*c*, one of which is normally closed by the valve member 48. That valve construction permits infusate to flow alternatively along two paths having different restriction characteristics or to two separate locations in the body. Similarly, the valve housing can be equipped with a variable volume chamber, e.g. a bellows in communication with cavity 24 and the valve inlet passage 42 made to terminate in the center of the upper housing member 22*b* at a valve seat similar to seat 38*a*. In such a valve, the valve member 48 may be biased to normally close the valve inlet passage, leaving the outlet passage 28 open. Then, by positioning a magnet outside the body opposite the valve so as to produce a bucking magnetic field, the valve member 48 is repelled so that it opens the valve inlet passage and closes the valve outlet passage. Thus a selected amount of infusate as determined by the available volume in the valve cavity 24 and variable volume chamber flows into the valve. Then, when the external magnet is removed, the valve member 48 returns to its rest position wherein it closes the valve inlet passage and opens the outlet passage permitting only that selected amount of infusate to flow to the infusion site. A valve of that type, then, operates both as a fluid switch and as a fluid metering device.

It should be appreciated also that other means besides magnet 78 can be utilized to provide the bias for the valve member 48. For example, in the FIG. 2 valve, one spring, say, spring 64 can be made with a higher spring constant than the spring 62 so that it tends to pull the valve member 48 toward the valve seat 38*a*. Also, in the case of a normally-closed valve, such as valve 10, the fluid pressure itself can serve as the biasing means, the amount of the bias being determined by the inlet pressure and the area of the seal 38.

Thus it will be seen from the foregoing that my valve has definite advantages over prior similar magnetically actuated valves of this general type.

Also, it will be apparent that the objects set forth above, among those made clear from the preceding description, are efficiently attained. Also, certain changes may be made in the above construction without departing from the scope of the invention. For example, the valve can be incorporated right into an implantable device such as reservoir 12. Therefore, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. A miniature implantable valve, said valve having
   A. a wafer-like housing defining a cavity,
   B. a first passage through a wall of the housing,
   C. a second passage through a wall of the housing,
   D. a valve seat formed in the housing between said passages,
   E. a movable ferromagnetic valve member positioned in the housing cavity,
   F. means for suspending the valve member within the cavity so that it is movable along a valve axis between a first position wherein it engages the valve seat and isolates said passages and a second position wherein the valve member is spaced away from the valve seat to permit fluid flow between said passages, said suspending means including
      1. a pair of substantially flat, wafer-like spiral spring members, each said spring member being relatively flexible in the direction perpendicular to the plane of the spring member but relatively stiff in the lateral direction in the plane of the spring member, and comprising a flat resilient plate having a plurality of substantially parallel narrow, equal-width spiral slits extending between the central portion of the plate and the outer edge margin thereof so as to form a plurality of flat spiral spring legs which are closely spaced and parallel along their entire lengths between the central portion of the spring member and its outer edge margin, 2. first means for securing the central portion of the spring member to one of said valve member and said housing, and 3. second means for securing the outer edge margin of the spring member to the other of said valve member and said housing so tht the valve member has a single degree of freedom of movement along the valve axis toward or away from the valve seat, and G. means for biasing the valve member toward one of said positions said biasing means comprising a ferromagnetic body mounted to the valve housing, at least one of said valve member and said body being axially polarized so as to produce a magnetic force which urges the valve member toward said one position.

2. The valve defined in claim 1 wherein the ferromagnetic valve member comprises an axially polarized permanent magnet.

3. The valve defined in claim 3 wherein the valve member comprises:
   A. a nonferromagnetic open container having a rim,
   B. an axially polarized permanent magnet positioned in the container, and
   C. a nonferromagnetic cover secured to the container rim to completely enclose the magnet within the container.

4. A miniature implantable valve, said valve having
   A. a wafer-like housing defining a cavity;
   B. a first passage through a wall of the housing;
   C. a second passage through a wall of the housing;
   D. a valve seat formed in the housing between said passages;
   E. a movable ferromagnetic valve member positioned in the housing cavity;
   F. means for suspending the valve member within the cavity so that it is movable along a valve axis between a first position wherein it engages the valve seat and isolates said passage and a second position wherein the valve member is spaced away from the valve seat to permit fluid flow between said passages, said suspending means including
      (1) a pair of substantially flat spring members, each said spring member
         (a) being relatively flexible in the direction perpendicular to the plane of the spring member,
         (b) being relatively stiff in the lateral direction in the plane of the spring member, and
         (c) comprising a flat resilient plate having a plurality of substantially parallel narrow equal-width spiral slits extending between the central portion of the plate and the outer edge margin thereof so as to form a plurality of parallel, flat, spiral spring legs whose side edges are closely spaced and parallel along their entire lengths between the central portion of the plate and the outer edge margin thereof,
      (2) first means for securing the central portion of the spring member to one of said valve member and said housing, and
      (3) second means for securing the outer edge margin of the spring member to the other of said valve member and said housing so that the valve member has a single degree of freedom of movement along the valve axis toward or away from the valve seat, and
   G. means for biasing the valve member toward one of said positions, said biasing means comprising a ferromagnetic body mounted to the valve housing, at least one of said valve member and said body being axially polarized so as to produce a magnetic force which urges the valve member toward said one position.

5. The valve defined in claim 4 wherein there are three such slits forming a triple-started spiral spring.

6. The valve defined in claim 5 wherein
   A. the corresponding ends of the slits are spaced at equal angles about the center of the plate, and
   B. each slit spirals about 360 degrees around the plate center.

7. The valve defined in claim 4 wherein there is a pair of said spring members secured to opposite faces of the valve member and to the valve housing so as to suspend the valve member centrally within the housing cavity.

8. A miniature transcutaneously magnetically actuated valve comprising
   A. a wafer-like housing defining a hollow cavity, said housing having
      1. a thickness of up to a half inch, and
      2. a total envelope volume of up to one-third of a cubic inch,
   B. first and second passages extending through the housing wall at spaced-apart locations therein,
   C. a valve seat separating said passages,
   D. a movable, wafer-like, ferromagnetic valve member positioned in the housing,
   E. means for suspending the valve member within the cavity so that it is movable along a valve axis between a first position wherein it engages the valve seat and isolates said passages and a second position wherein the valve member is spaced away from the valve seat to permit fluid flow between said passages, siad suspending means including a pair of substantially flat, wafer-like spiral spring members, each said spring member being relatively flexible in the direction perpendicular to the plane of the spring member but relatively stiff in the lateral direction in the plane of the spring member, and comprising a flat resilient plate having a plurality of substantially parallel narrow, equal-width spiral slits extending between the central portion of the plate an the outer edge margin thereof so as to form a plurality of flat spiral spring legs which are closely spaced and parallel along their entire lengths between the central portion of the spring member and its outer edge margin.
   F. means for biasing the value member in one direction, and
   G. ferromagnetic means operable transcutaneously for moving the value member in the other direction in opposition to the biasing means.

* * * * *